(12) United States Patent
Pandey (10) Patent No.: US 8,088,138 B2
(45) Date of Patent: Jan. 3, 2012

(54) SURGICAL TOOL

(75) Inventor: Rajesh Pandey, Plantation, FL (US)

(73) Assignee: Heartware, Inc., Miami Lakes, FL (US)

( * ) Notice: Subject to any disclaimer, the term of this patent is extended or adjusted under 35 U.S.C. 154(b) by 741 days.

(21) Appl. No.: 11/337,708

(22) Filed: Jan. 23, 2006

(65) Prior Publication Data

US 2007/0173879 A1 Jul. 26, 2007

(51) Int. Cl.
*A61B 17/00* (2006.01)

(52) U.S. Cl. ......... 606/190; 606/185; 606/167; 606/108

(58) Field of Classification Search ............... 128/303 R; 604/51, 507, 272, 49, 8; 606/151, 190, 185, 606/167, 108, 148; 600/29, 30, 37; 403/342, 403/343, 296, 307
See application file for complete search history.

(56) References Cited

U.S. PATENT DOCUMENTS

| | | | |
|---|---|---|---|
| 3,908,637 A * | 9/1975 | Doroshow | 600/573 |
| 4,509,516 A | 4/1985 | Richmond | |
| 4,832,687 A | 5/1989 | Smith, III | |
| 5,306,240 A * | 4/1994 | Berry | 604/507 |
| 5,579,668 A | 12/1996 | Kozak | |
| 5,607,443 A | 3/1997 | Kieturakis | |
| 5,667,510 A * | 9/1997 | Combs | 606/86 R |
| 5,782,841 A | 7/1998 | Ritz et al. | |
| 6,468,219 B1 | 10/2002 | Njemanze | |
| 6,475,244 B2 | 11/2002 | Herweck et al. | |
| 6,605,094 B1 * | 8/2003 | Mann et al. | 606/129 |
| 6,911,003 B2 | 6/2005 | Anderson et al. | |
| 7,267,645 B2 * | 9/2007 | Anderson et al. | 600/30 |
| 2003/0045892 A1 | 3/2003 | Kaladelfos | |
| 2003/0050530 A1 * | 3/2003 | Neisz et al. | 600/29 |
| 2004/0044348 A1 | 3/2004 | Skakoon | |
| 2004/0106845 A1 * | 6/2004 | Anderson et al. | 600/30 |
| 2006/0135949 A1 * | 6/2006 | Rome et al. | 604/533 |
| 2007/0088343 A1 | 4/2007 | McIntyre et al. | |
| 2007/0129719 A1 | 6/2007 | Kendale et al. | |

OTHER PUBLICATIONS

International Search Report issued by the International Searching Authority (ISA/US) on Sep. 25, 2007 in connection with International Application No. PCT/US2007/00174.

Written Opinion of the International Searching Authority issued by the International Searching Authority (ISA/US) on Sep. 25, 2007 in connection with International Application No. PCT/US2007/001743.

(Continued)

*Primary Examiner* — Ryan Severson
*Assistant Examiner* — Tin Nguyen
(74) *Attorney, Agent, or Firm* — John P. White; Cooper & Dunham LLP (57) ABSTRACT

A tunneling device for creating a pathway in subcutaneous tissue of a person's body. The tunneling device includes a member having two ends, where each of the ends defines an insertion surface that facilitates the insertion of the ends into the subcutaneous tissue of the person's body. The tunneling device includes an interchangeable handle connectable to each of the ends. The handle defines a grasping surface and an opening. The opening is configured to receive either of the ends. The grasping surface enables a user to securely hold the handle with one hand to forcibly move the member through the subcutaneous tissue of the person's body to create the pathway in the subcutaneous tissue, and pull a cable of an implant device through the created pathway.

20 Claims, 7 Drawing Sheets

OTHER PUBLICATIONS

International Preliminary Report on Patentability issued by the International Bureau of WIPO in connection with International Application No. PCT/US07/01743.

Written Opinion of the International Searching Authority issued by the International Searching Authority (ISA/US) in connection with International Application No. PCT/US07/01743.

International Search Report issued by the International Searching Authority (ISA/US) in connection with International Application No. PCT/US2008/09016.

Written Opinion of the International Searching Authority issued by the International Searching Authority (ISA/US) in connection with International Application No. PCT/US2008/09016.

* cited by examiner

SURGICAL TOOL

BACKGROUND

Thousands of heart patients who suffer from severe heart failure could benefit from a heart transplant. However, because of a shortage of donor hearts, most of these patients face a shortened life span characterized by frequent hospitalizations, severe physical disability, and death from congestive failure or cardiogenic shock.

One medical device developed to aid these heart patients is a heart pump such as a left ventricular assist device which enables heart failure patients to return to prolonged and productive lives. A left ventricular assist device ("LVAD") is a battery-operated, mechanical pump-type device that is surgically implanted. It helps maintain the pumping ability of a heart that cannot effectively work on its own.

A LVAD typically includes an electrical cable which is hardwired into the LVAD and routed through a patient's body to an external controller and battery. The surgical procedure of creating a channel or "tunnel" for routing the electrical cable through the body is commonly called "tunneling."

The "tunneling" procedure is an invasive procedure that can lead to infection. Therefore, to minimize the risk of infection and to provide a secure mechanical attachment between the electrical cable and the surrounding tissue, the tunneling channel or path is typically made smaller in size than the electrical connector attached at an end of the electrical cable. The electrical connector is the part of the electrical cable that plugs into or engages the external controller. Usually, the electrical connector is larger in size than the flexible body portion of the electrical cable. As a result, the force required to physically pull the electrical cable through a patient's body is relatively high.

The surgical procedures for creating a tunneling channel or path in a patient's body varies widely. In one procedure, commonly called the outside-in procedure, the tunneling path is created by a tunneling tool, which starts forming the tunnel on the outside of the patient's body. The tunnel goes through the abdominal cavity and up into the thoracic cavity near the LVAD and heart. After the tunnel or pathway is made in the patient's body, the electrical cable is tied to the tunneling tool by a suture or other means. The electrical cable is then dragged or pulled back through the tunneling path using the tunneling tool until a suitable length of the electrical cable extends from the patient's body to connect the electrical cable to the external controller.

In another procedure, commonly called the inside-out procedure, the tunneling path is started from the thoracic cavity inside of the patient's body and continues out through the patient's abdomen and skin to outside of the patient's body. The electrical cable is tied or otherwise connected to the end of the tunneling tool inside the body and pulled through the path to outside the body.

Both of the tunneling procedures described above and other similar procedures employ a relatively high force to pull or drag the electrical cable through the tunnel or path formed in the patient's body. The high stress on the tissues of the body cause trauma to the issues and could lead to complications, infection and extended recovery time for patients.

Additionally, depending on which procedure is used, the design of the tunneling tool may be suitable for one procedure such as the outside-in procedure, but not suitable or usable for another procedure, such as the inside-out procedure.

Accordingly, there is a need for a surgical tool which is adaptable to be used for different tunneling procedures, which is easy to manipulate and use during a tunneling procedure and which minimizes the stress on the body and the risk of infection during the procedure.

SUMMARY

The present invention is directed to a surgical tool and, more specifically, to a surgical tunneling device for creating a pathway in the subcutaneous tissue of the body which is easy to use and adaptable for use in different tunneling procedures.

One embodiment of the present invention provides a tunneling device that includes a malleable member having two ends, where each of the ends defines an insertion surface that facilitates the insertion of the ends into the subcutaneous tissue of the person's body. The tunneling device includes an interchangeable handle connectable to each of the ends. The handle defines a grasping surface and an opening. The opening is configured to receive either of the ends. The grasping surface enables a user to securely hold the handle with one hand to forcibly move the malleable member through the subcutaneous tissue of the person's body to create the pathway in the subcutaneous tissue, and pull a cable of an implant device through the created pathway.

In an embodiment, the tunneling device includes a tip removably connected to at least one of the ends. The tip defines an insertion surface.

In an embodiment, the tunneling device includes a tip removably connected to each of the ends. The tips respectively defining the insertion surface, where at least a portion of each of the ends defines a plurality of threads, and where each of the tips is threadingly engaged with one of the ends of the malleable member.

In an embodiment, the insertion surface defined by at least one of the ends is a tapered surface.

In an embodiment, the insertion surface defined by each of the ends is a tapered surface.

In an embodiment, the tunneling device includes a coupler removably connected to one of the ends of the member. The coupler is adapted to couple the malleable member to an end of the cable.

In an embodiment, the handle includes an actuator, where the actuator is operable to cause the handle to engage with or disengage from one of the ends.

In an embodiment, the handle includes a shaft and a spring positioned between the shaft and the actuator. The actuator is operable to compress the spring and cause the shaft to move to a position where one of the ends of the malleable member is insertable into or releasable from the handle.

Another embodiment provides a tunneling system for creating a pathway in subcutaneous tissue of a person's body. The tunneling system includes a malleable member having a first end and a second end. Each of the ends defines an insertion surface that facilitates the insertion of the first and second ends into the subcutaneous tissue of the person's body. The tunneling device includes an interchangeable handle connectable to each of the first and second ends. The handle defines a grasping surface and an opening. The opening is configured to receive either of the first and second ends and the grasping surface enables a user to securely hold the handle with one hand. The tunneling system also includes a coupler operable to join one of the first and second ends of the malleable member and an end of a cable of an implant device to secure the malleable member and the cable together. The handle is operable to enable a user to forcibly move the malleable member through the subcutaneous tissue of the person's body to create the pathway in the subcutaneous tissue and enable the user to pull the cable of the implant device through the created pathway.

In an embodiment, the handle includes a post and a spring positioned between the post and the actuator. The post has a first diameter and a second smaller diameter. The post is initially positioned adjacent to the first end of the malleable member inserted in the handle to prevent the first end from being removed from the handle. The spring biases the post inwardly to cause the second diameter of the post to be positioned adjacent to the first end of the malleable member to enable the first end of the malleable member to be removed from the handle.

In an embodiment, the insertion surface of at least one of the first and second ends is a tapered surface.

In an embodiment, the insertion surface of each of the first and second ends is a tapered surface.

In an embodiment, the tunneling system includes a removable tip attached to each of the first and second ends, where the removable tips respectively define the insertion surface described above.

In an embodiment, the insertion surface of at least one of the tips is a tapered surface.

In an embodiment, the insertion surface of each of the tips is a tapered surface.

In an embodiment, at least a portion of each of the tips defines a plurality of threads, where each of the tips is threadingly engaged with one of the ends of the member.

In an embodiment, the coupler includes a plurality of connectors. A first connector of the plurality of connectors is operable to secure the coupler to the end of the cable and a second connector of the plurality of connectors is operable to secure one of the first and second ends of the malleable member to the coupler.

Another embodiment provides a method of forming a pathway in subcutaneous tissue of a person's body. The method includes providing a malleable member having two ends, where each of the ends is insertable into the subcutaneous tissue of the person's body. The method includes providing a handle connectable to each of the ends of the member. The handle including an actuator operable to cause the handle to be engaged with and disengaged from one of the ends of the member. The method includes activating the actuator, connecting the handle to one of the ends of the malleable member and inserting the other of the ends into the subcutaneous tissue of the person's body. The method includes moving the other of the ends through the subcutaneous tissue of the person's body to create the pathway in the tissue of the body and connecting a cable of a medical device implanted in the body to the other of the ends. The method includes moving the cable through the pathway created in the body using the handle.

In an embodiment, the method includes connecting a coupler to one of the ends of the malleable member and to an end of the cable.

In an embodiment, the method includes connecting a removable tip to each of the ends. Each of the removable tips defining an insertion surface to facilitate the movement of the tips through the subcutaneous tissue of the body.

It is therefore an advantage of the present invention to provide a surgical tunneling device which enhances the efficiency of a surgical procedure.

Another advantage of the present invention is to provide a surgical tunneling device which is adaptable to be used for different tunneling procedures.

Other objects, features and advantages of the invention will be apparent from the following detailed disclosure, taken in conjunction with the accompanying sheets of drawings, wherein like numerals refer to like parts, elements, components, steps and processes.

DETAILED DESCRIPTION

The present invention is directed to a surgical tool, and more specifically, to a tunneling device which creates a pathway in the subcutaneous tissue of a person's body for routing cables of an implant device outside of the person's body to allow the communication with and delivery of power to the implant device.

Referring now to the figures, the tunneling device 100 of the present invention includes a flexible or malleable shaft or malleable member 102 which is semi-rigid and bendable to curve or bend through the tissue of a person's body. The malleable member is made of a bendable or flexible material such as 6061 anodized aluminum or any other suitable material or combination of materials. The malleable member 102 may be any suitable size in shape and is generally sized to be slightly smaller than the size or diameter of a cable or wire connected to an implant device, which is routed through a person's body. In the illustrated embodiment, the malleable member 102 includes two ends 104a and 104b. In one embodiment, each of the ends 104a and 104b are identical and define an insertion surface which is angled or tapered to facilitate the insertion of the ends into tissue of a person's body.

In one embodiment, a tapered or bullet-like interchangeable removable tip 106 is connected to at least one of the ends 104a and 104b. In another embodiment, the removable tip 105 is connected to each of the ends 104a and 104b. Each tip 105 includes an angled or tapered surface 106 which defines the insertion surface to facilitate the insertion or piercing and movement of the tips through the subcutaneous tissue of the body. In the illustrated embodiment, the tips 105 are made of stainless steel. It should be appreciated that the tips may be made of any suitable material or materials.

Figure 4:
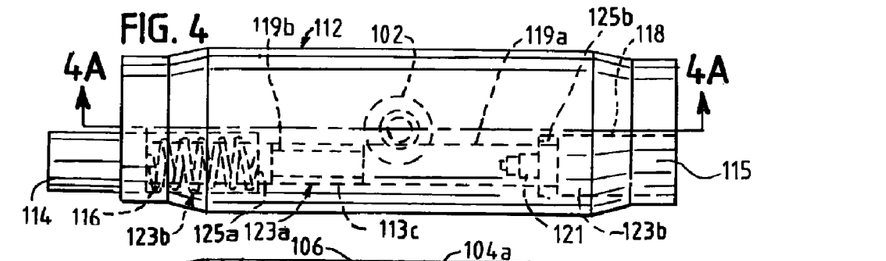
FIG. 4 is a top view of the surgical tool of FIG. 1 where certain parts of the handle and an end of the flexible malleable member are shown in phantom.
Figure 4A:
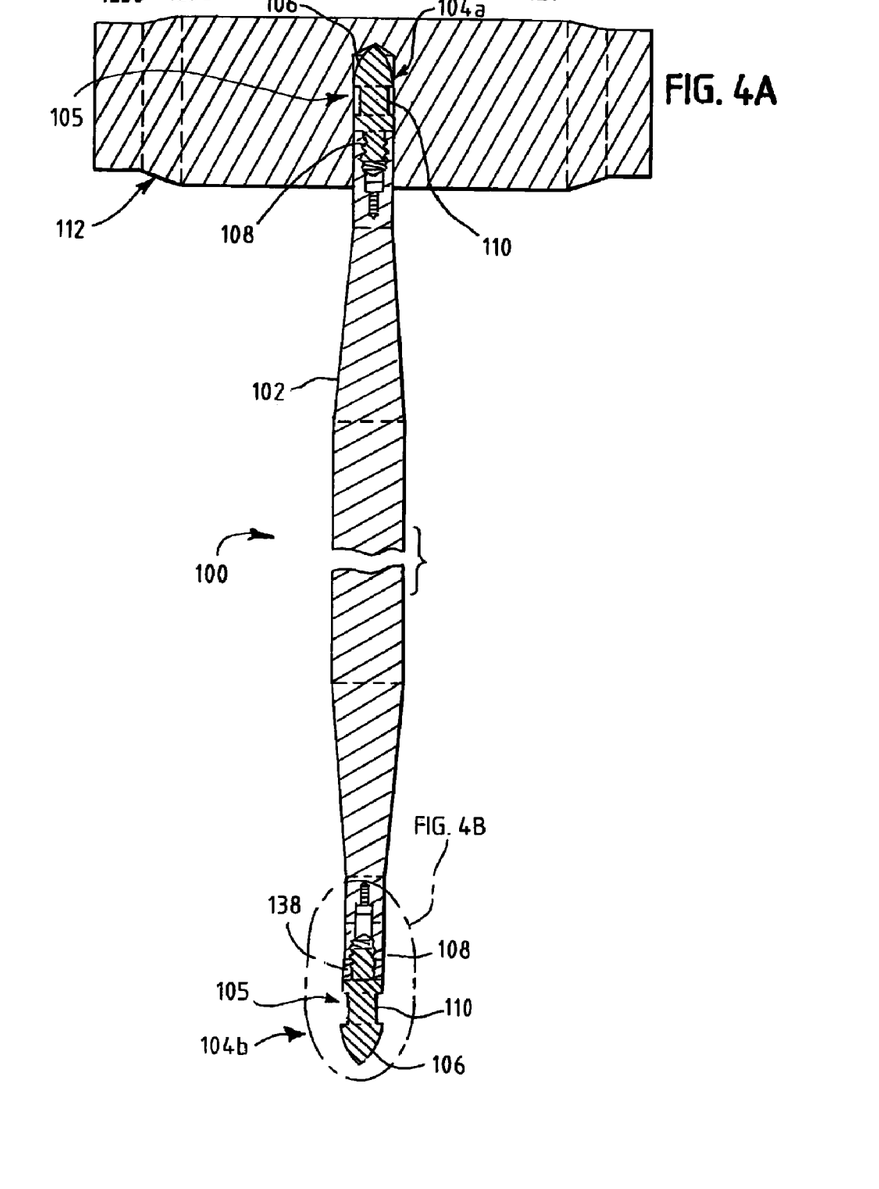
FIG. 4A is a cross section view taken substantially along line 4A-4A of FIG. 4.
Figure 4B:
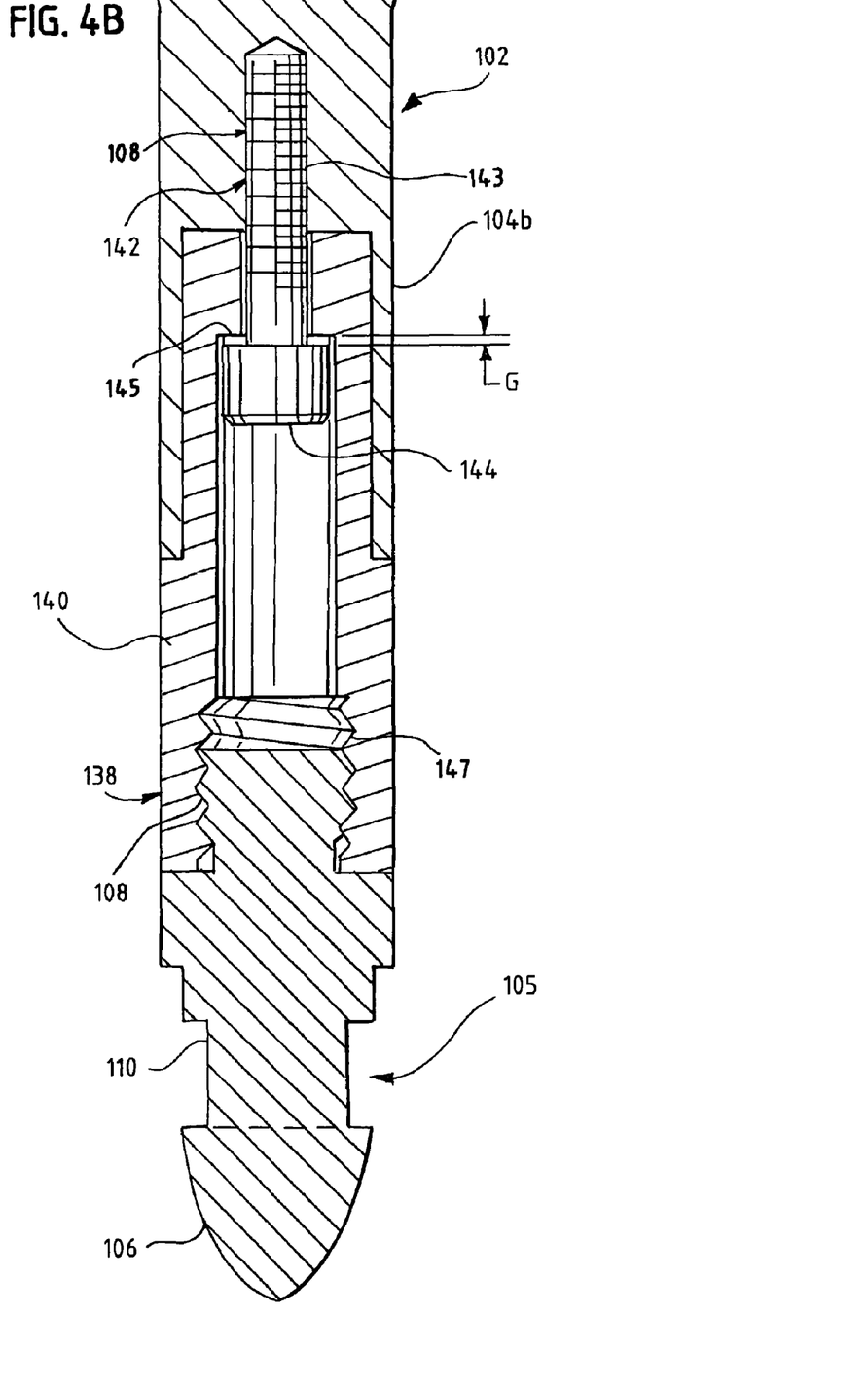
FIG. 4B is an enlarged fragmentary view of an end of the surgical tool shown in FIG. 4A.
Figure 4C:
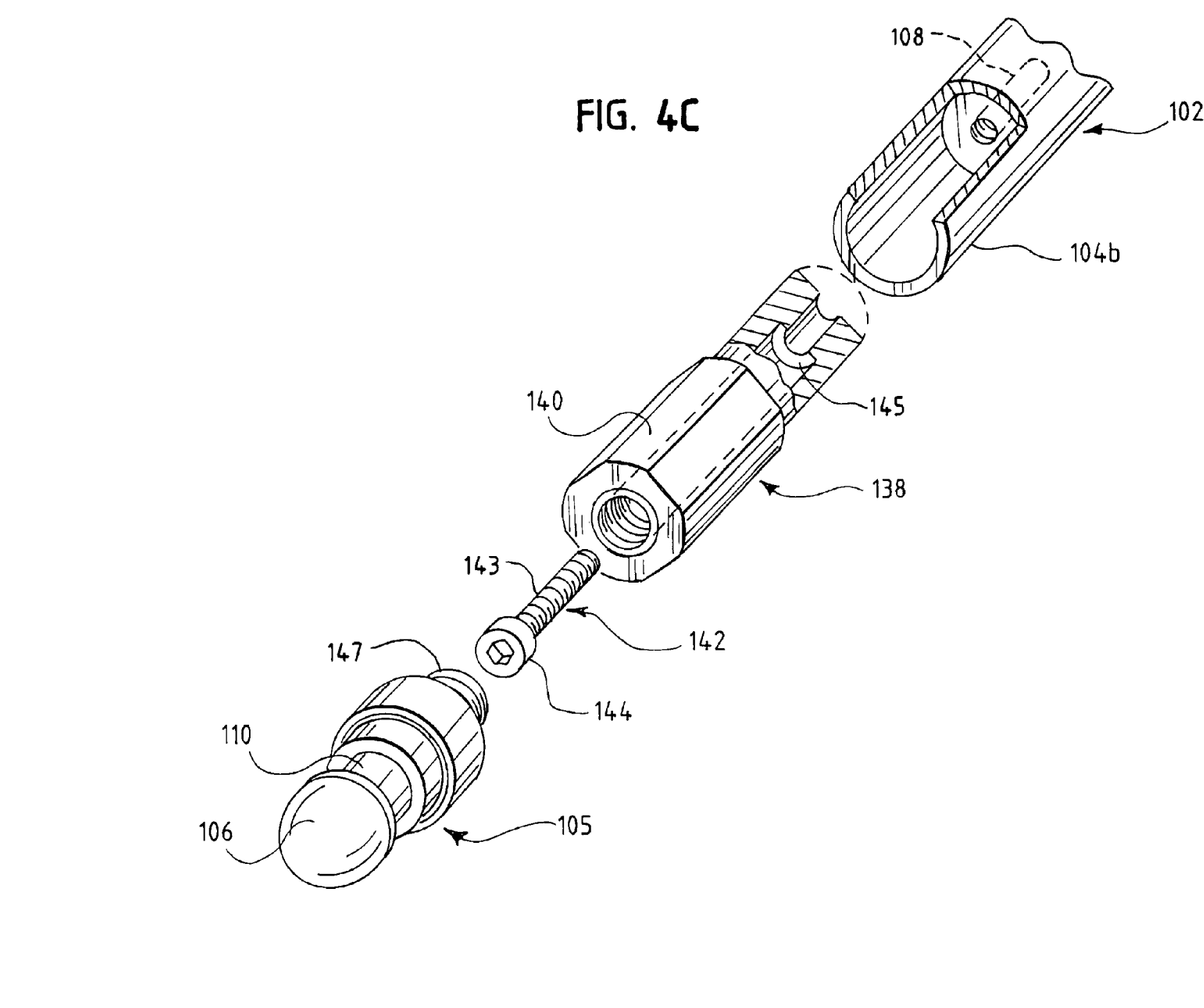
FIG. 4C is a fragmentary exploded view of an end of the surgical tool shown in FIG. 4A.
Figure 5A:
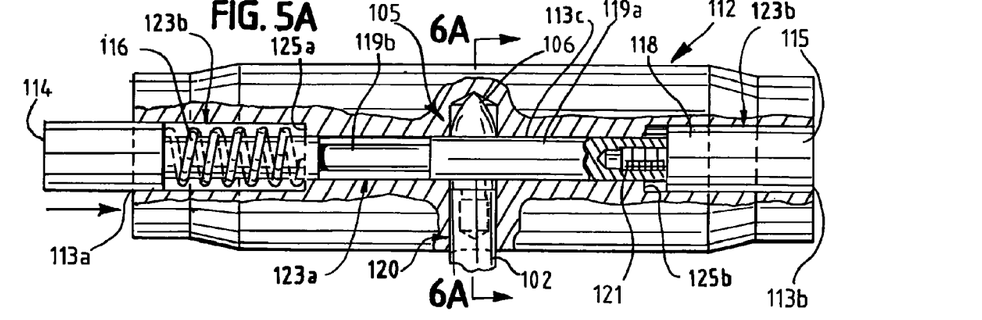
FIG. 5A is a partial cut away top view of the surgical tool of FIG. 1 illustrating an end of the flexible malleable member engaged with the handle.
Figure 5B:
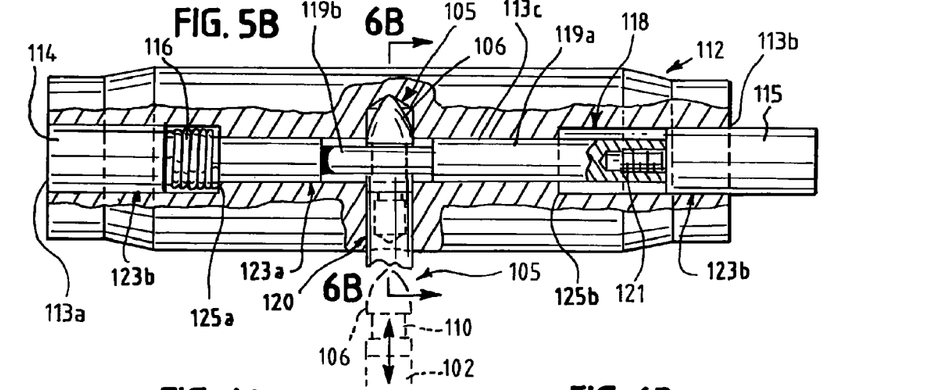
FIG. 5B is a partial cut away top view of the surgical tool of FIG. 1 illustrating the end of the flexible malleable member disengaged from the handle.
Figure 6A:
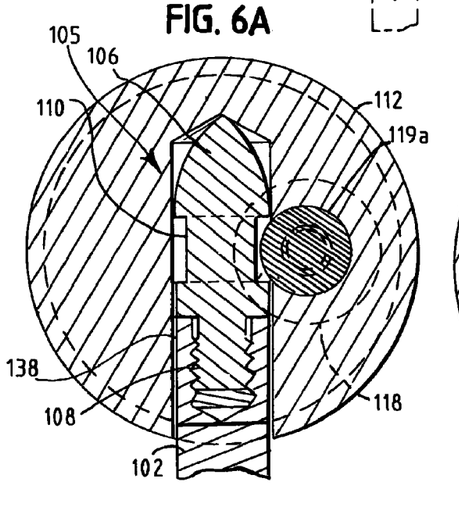
FIG. 6A is a cross-section view taken along line 6A-6A in FIG. 5A illustrating the handle engaged with the end of the malleable member.
Figure 6B:
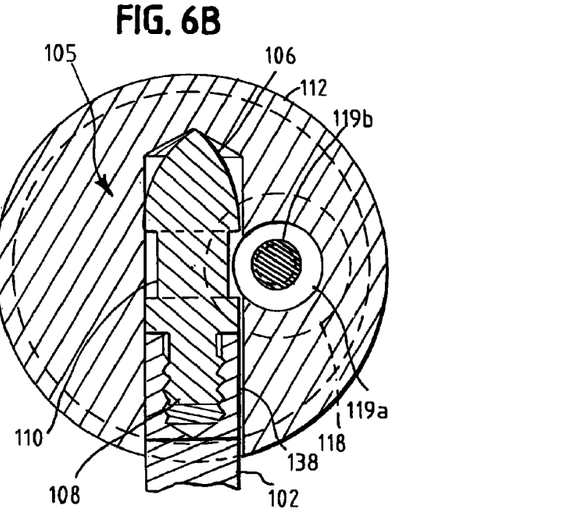
FIG. 6B is a cross-section view take substantially along line 6B-6B in FIG. 5B illustrating the handle disengaged from the end of the malleable member.

Referring to FIGS. 4B and 4C, each end 104a and 104b includes a threaded portion 108 which is threadingly engaged with corresponding threads 142 formed on a portion of the tips 106. Specifically, a cap screw 142 is inserted into an end of the removable tip. The cap screw 142 includes a threaded portion 143 and a head 144. The threaded portion 143 extends through an opening defined by rotating collar 138 and is screwed into the corresponding threaded portions 108 of one or both ends 104a and 104b to hold or secure the collar 138 to the ends 104a and 104b. The cap screw is twisted or screwed into the end of the malleable member 102 so that a gap, G, is formed between the bottom of the head 144 of the cap screw 142 and bottom inside surfaces of the collar 138 as shown in FIG. 4B to allow the collar 138 to freely move or rotate with respect to the end of the malleable member. It should be appreciated that the gap, G, may be any suitable size to allow free rotation of the collar.

The tip 105 defines threads 147 and is screwed into corresponding threads defined by the collar 138 to enable the tips 105 to be secured to the ends 104a and 104b of the malleable member 102. In one example, the tip 105 is screwed into the collar 138 by rotating the tip and holding the collar in place. In another example, the tip 105 is held in place while a user grasps or grips beveled surfaces 140 of the collar 138 and rotates the collar 138 using their fingers or a tool to secure the collar 138 to the cap screw 142. It should be appreciated that the tip 105 may be secured to the collar 138 or the ends 104a and 104b using any suitable connector or connection method.

Figure 1:
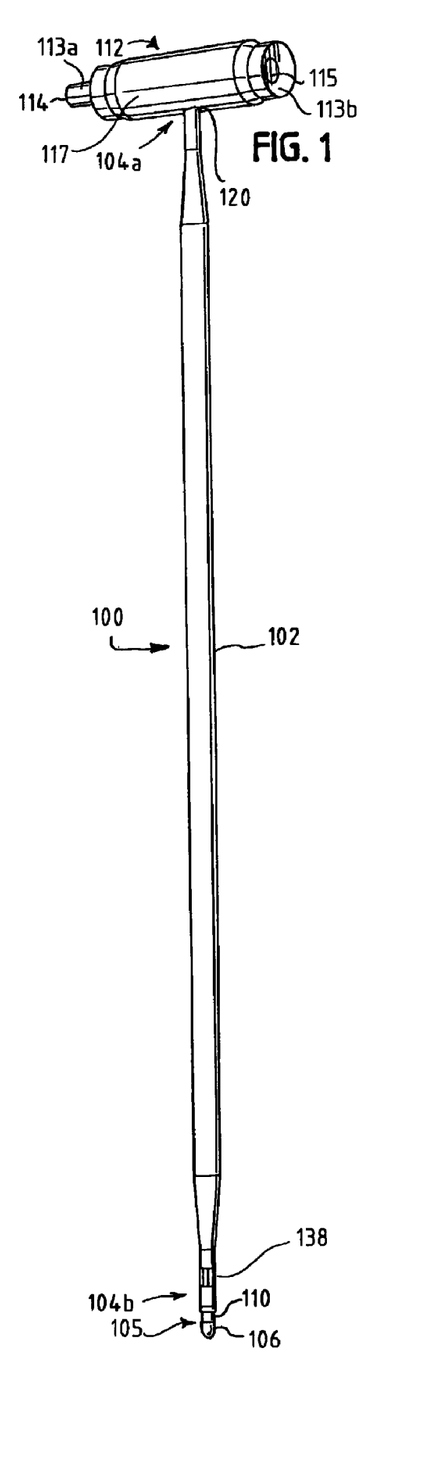
FIG. 1 is a perspective view of one embodiment of the surgical tool of the present invention.
Figure 2:
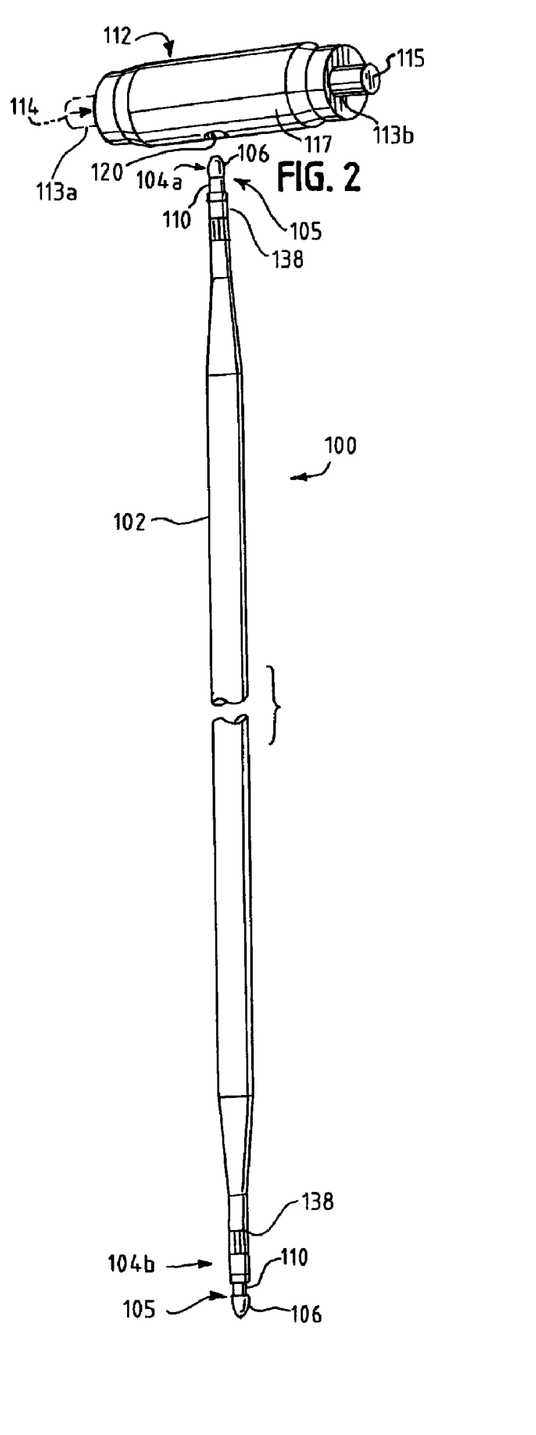
FIG. 2 is a fragmentary exploded view of FIG. 1.
Figure 3:
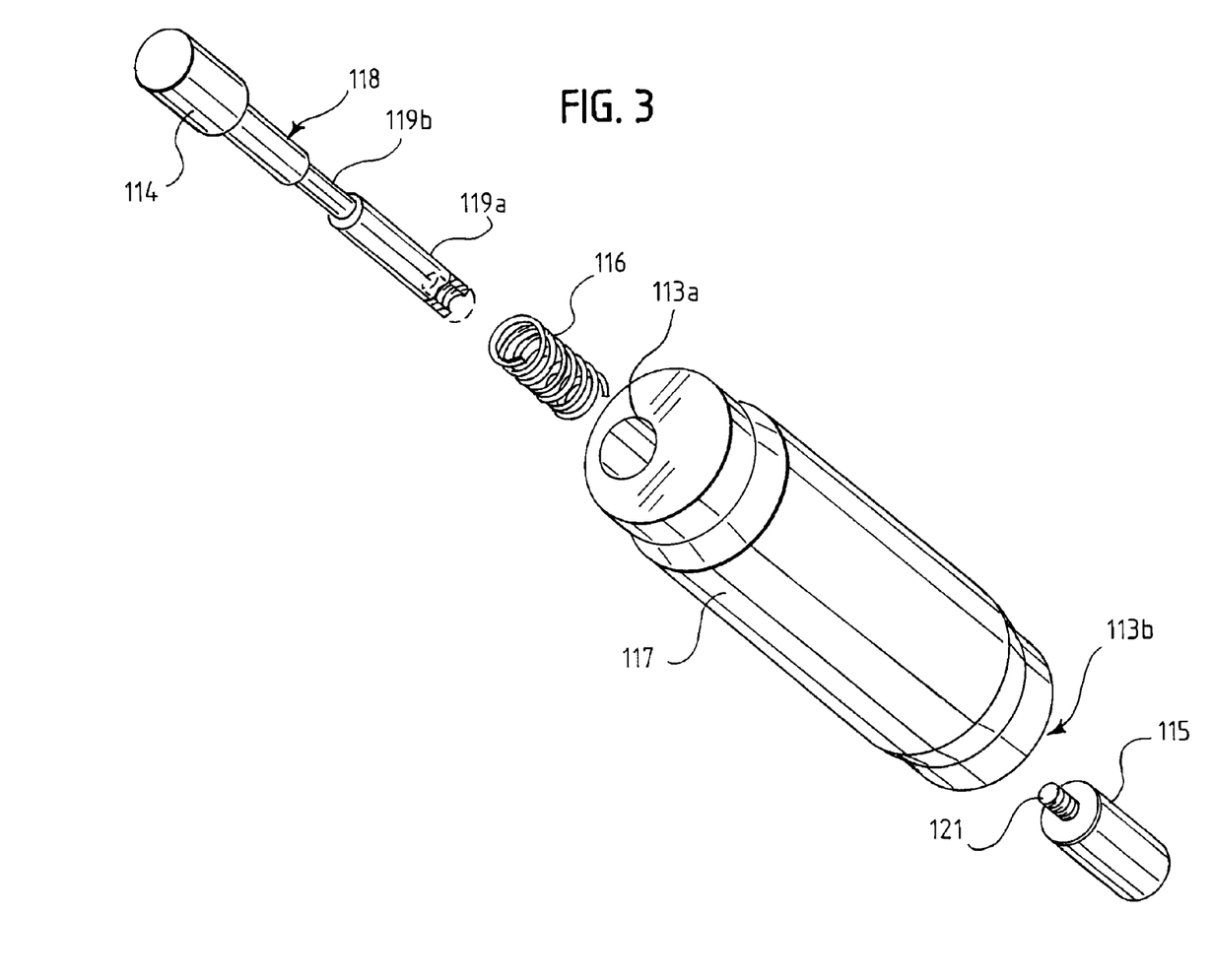
FIG. 3 is an exploded view of the handle shown in FIG. 1.

Referring to FIGS. 3-6B, the handle or grip 112 is connectable to each end 104a and 104b and more specifically, to each tip 106 connected to the ends of the malleable member 102. The handle 112 includes an input, button or actuator 114, a spring 116 positioned adjacent to the actuator and an engagement shaft or post 118 which is positioned adjacent to the spring 116. The handle defines an opening 120 which is positioned on an axis that is transverse to the axis defined by the engagement shaft or post. As shown in FIG. 3, the handle defines end openings 113a and 113b and channel 113c. In one embodiment, the handle 112 is made of 6061 anodized aluminum. It should be appreciated that the handle may be made of any suitable material or materials.

The channel 113c is an elongated opening which extends the length of the handle and includes an axis which is parallel to the axis of the handle. The channel 113c is positioned off-center as shown in FIG. 4. It should be appreciated that the channel 113c may extend along the center of the handle or along any suitable position on the handle. In the illustrated embodiment, the channel 113c includes a central portion or area 123a having a first diameter and end portions or areas 123b each having a second larger diameter than the first diameter. In the illustrated embodiment, the diameters of end portions 123b are the same. In another embodiment, the diameters of the end portions 123b are different. In the illustrated embodiment, the end portions 123b each define a shoulder 125. Specifically, as shown in FIG. 4, one end portion defines shoulder 125a and the opposing end portion defines shoulder 125b.

FIGS. 3 and 4 illustrate the assembly of the handle 112. The button 114 and post 118 are connected together. In one embodiment, the button 114 and post 118 are separate parts which are connected together using any suitable connector or connection method. In another embodiment, the button 114 and post 118 are integrally formed. In the illustrated embodiment, the post 118 is inserted through spring 116 and into the end opening 113a. The post 118 is inserted through channel 113c and is secured in place by cap 115 which is connected to an end of post 118. The cap 115 includes a threaded portion or post 121 which is threadingly engaged with the end of post 118 as shown in FIG. 4. The spring 116 is positioned between the button 114 and shoulder 125a. Shoulder 125a provides a bearing surface for spring 116 so that spring 116 compresses when button 114 is pushed or pressed inwardly and expands when button 114 is released or moves outwardly away from housing 117. Shoulder 125b acts as a stop to prevent cap 115 from moving inwardly past a predetermined distance in housing 117. The position of shoulder 125b determines the distance that button 114 extends from housing 117.

In the illustrated embodiment, the post 118 includes a first diameter 119a and a second diameter 119b. In one embodiment, the first diameter is larger than the second diameter. It should be appreciated that the post may have any suitable number of diameters and the diameters may be the same or different. The handle further defines a grasping or holding surface 117 which is grasped by a user's hand to forcibly push or pull the malleable member 102.

Referring to FIGS. 4, 4A, 4B, 4C, 5A, 5B, 6A and 6B, the opening 120 is adapted to receive one of the ends of the malleable member 102. The end and more specifically, a designated length of the tip 106 connected to the end, is inserted into the opening 120. Once the tip 106 is inserted into the opening 120 of the handle 112, the actuator or button 114 is released and the spring 116 biases the actuator 114 outwardly away from the handle 112. This causes the engagement shaft or post 118 to move in the same direction as the actuator and causes the first diameter 119a of the shaft or post to engage the groove 110 defined by the tip 106 connected to the malleable member 102. The first diameter 119a of the engagement shaft or post 118 engages the groove 110 defined by the tip 106 in such a way that the tip 106 of the malleable member 102 cannot be pulled out of the opening 120 defined by the handle 112. As a result, the end 104a and more specifically, the tip 106 of the malleable member 102 is secured to the handle 112. To release the tip 106 from the handle 112, the button or actuator 114 is activated or pressed to cause the spring 116 to bias the post 118 inwardly within the handle 112. This causes the smaller second diameter section 119b of the post 118 to be positioned over the tip 106 of the malleable member 102. Because the smaller second diameter 119b of the post 118 does not engage the groove 110, the tip 106 of the malleable member 102 is free to move outwardly away from the opening 120 of the handle 112 to be released or removed from the handle. When the end 104a is removed from the handle 112, the button 114 is de-activated or released.

Figure 7A:
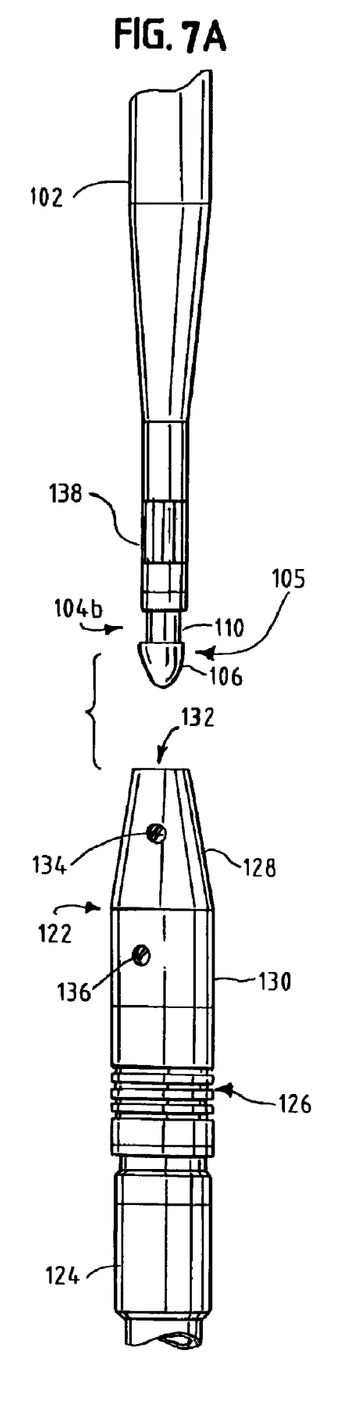
FIG. 7A is a partial side view of the surgical tool of FIG. 1 and an electrical cable illustrating an end of the flexible malleable member of the surgical tool disengaged from an end of the electrical cable.
Figure 7B:
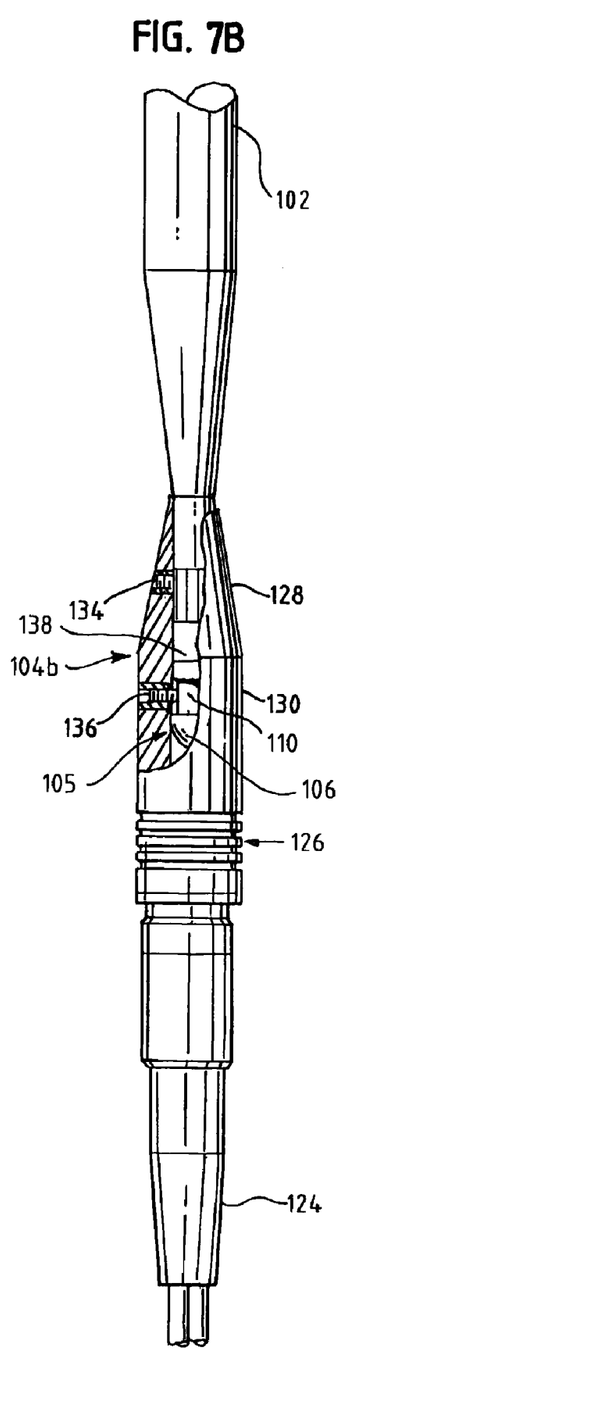
FIG. 7B is a partial side view of the surgical tool of FIG. 1 and an electrical cable illustrating an end of the flexible malleable member of the surgical tool engaged with the end of the electrical cable.

Referring now to FIGS. 7A and 7B, a cap, coupler or coupling device 122 is connected to an end 126 of a cable such as an electrical cable associated with an implant device inserted in a person's body to enable one of the tips 106 of the malleable member 102 to be connected or coupled to the cable 124 to move, pull or push the cable through a tunnel or pathway created by the tunneling device 100 in the body and to minimize or prevent tissues and other contaminants from accumulating on an end of the cable. The coupler 122 includes an angled or tapered portion 128 which defines an opening 132 to receive the end 104b of the malleable member 102. The coupler 122 also includes a straight portion or bottom portion 130 which includes a set screw 134. The set screw 134 is turned or tightened after the coupler 122 is inserted on the end 126 of the cable 124 to secure the coupler to the cable. The end 104b of the malleable member 102 is inserted through the opening 132 defined by the coupler and is secured by a set screw 136 threadingly connected to an inside surface at the tapered portion 128 of the coupler. The set screw 136 is turned and tightened to engage the set screw 136 with the groove 110 formed or defined by the tip 106 of the malleable member 102 to secure the malleable member 102 to the coupler 122. Once secured, the tunneling device 100 can be used to move, push or pull cable 124 through a tunnel path formed in the tissue of the body using the tunneling device 100.

In operation, the tunneling device 100 of the present invention may be used regardless of the surgical procedure employed to create the tunnel or pathway in the tissue of a person's body. For example, the tunneling device 100 may be used to form a tunneled pathway for an inside-out procedure or for an outside-in procedure, as described above. In the outside-in procedure, an end 104a or 104b of the malleable member 102 is inserted into the tissue of a patient's body. The handle 112 is then inserted on the end 104a or 104b of the malleable member 102 that is not inserted into the tissue of the body by pressing or activating the button 114 on the handle 112 and inserting the end of the malleable member 102 into the opening 120 defined by the handle 112. The button 114 is released to secure the handle 112 to the end of the malleable member 102 as described above. The handle 112 is attached to an end 104a or 104b, and more specifically, one of the tips 106 of the malleable member 102 using a single hand which saves time during the surgical procedure.

When the handle 112 is secured to the malleable member 102, a user applies a force to the handle 112 to push the handle 112 inwardly towards the body to cause the inserted end 104a or 104b, and more specifically, the tip 106 of the malleable member 102 to move through the tissue of the body. Once the inserted end of the malleable member 102 reaches the thoracic cavity, the cable 124 of the implant device (not shown) such as a blood pump, is connected to the end of the malleable member 102 using the coupler 122 as described above. When the cable 124 is coupled to the malleable member 102 of the tunneling device 100, the user holds onto the grasping surface 117 of the handle and pulls the handle away from the body to correspondingly pull the inserted end 104a or 104b, or tip 106 of the malleable member 102 and the coupled cable 124 through the tunneled pathway. The cable 124 is pulled through the tunneled pathway by the tunneling device 100 until the cable is pulled a sufficient distance out of the patient's body so that the cable can be connected to a suitable controller, battery or the like.

In an inside-out procedure, one of the tips 106 of the malleable member 102 is inserted into the tissue near the thoracic cavity by the heart. The handle 112 is secured to the opposite end or tip of the malleable member (i.e., the end or tip not inserted in the tissue), as described above. The handle 112 is then pushed or forced inwardly until the inserted end or tip of the malleable member 102 exits the body through the skin. The handle 112 is then removed by pressing or activating the button 114 to release the handle from the opposite end or tip of the malleable member 102. The handle 112 is then connected on the other end of the malleable member 102 (i.e., the inserted end) by pressing the button 114 and inserting that end or tip of the malleable member 102 into the opening 120 defined by the handle 112. The present invention therefore enables the tunneling device 100 to be used for any surgical tunneling procedure to create a tunnel or pathway in the patient's body. In this procedure, the cable 124 is coupled to the malleable member near the thoracic cavity, and the cable 124 is pulled through the body by pulling on the handle as described above. The tunneling device 100 of the present invention is adaptable to be used in any surgical procedure for creating a tunnel or pathway in the tissue of the body. The tunneling device 100 of the present invention also enables a user to employ a one-handed operation which saves valuable time during a surgical procedure.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims, and this application is limited only by the scope of the claims.

The invention is claimed as follows:

1. A tunneling device for creating a pathway in subcutaneous tissue of a person's body, said tunneling device comprising:
   a malleable member having a first end and a second end, each of said first end and said second end of said malleable member including an axial, internal thread;
   a first collar rotatably fastened to said first end of said malleable member allowing rotation of said first collar about a longitudinal axis of said first end;
   a cap screw having a head and a shaft, said shaft coupled with said axial, internal thread and a protruding portion of said shaft extending from said axial, internal thread to said head;
   said first collar having a clearance hole extending through a portion of said first collar and including threads opposite said clearance hole; and
   a first tip threaded into said threads of said first collar, the protruding portion of said shaft extending through said clearance hole to rotatably fasten said first collar to said first end of said malleable member; and
   a handle configured to removably connect to said tunneling device,
   said handle including a grasping surface and an opening, said opening configured to receive said first tip to removably connect said handle to said first tip,
   said grasping surface configured to allow a user to securely hold the handle with one hand to forcibly move said malleable member through the subcutaneous tissue of the person's body,
   said first collar allowing the user to draw a cable into a surgical tunnel using said tunneling device with the risk of applying rotational torque to said cable being reduced.

2. The tunneling device of claim 1, wherein said malleable member further includes at least one tapered insertion surface adjacent to at least one of said first end and said second end.

3. The tunneling device of claim 1, wherein said malleable member further includes a first tapered insertion surface adjacent to said first end and a second tapered insertion surface adjacent to said second end.

4. The tunneling device of claim 1, further comprising:
   a second collar rotatably fastened to said second end of said malleable member allowing rotation of said second collar about a longitudinal axis of said second end; and
   a second tip fastened to said second collar.

5. The tunneling device of claim 4, in which said handle is connected to one of said first tip and said second tip.

6. The tunneling device of claim 4, further comprising: a coupler removably connected to one of said first tip and said second tip, said coupler adapted to couple said malleable member to an end of said cable.

7. The tunneling device of claim 4, wherein at least one of said first and said second tips include a tapered surface.

8. The tunneling device of claim 4, wherein each of said first and said second tips include a tapered surface.

9. The tunneling device claim 4, further comprising a coupler configured to join one of said first tip and said second tip and an end of a cable of an implant device securing said malleable member and said cable together, said coupler including a plurality of connectors, a first connector of said plurality of connectors configured to secure said coupler to said end of said cable, and a second connector of said plurality of connectors configured to secure one of said first tip and said second tip to said coupler.

10. The tunneling device of claim 4, wherein said first and second tips each include an annular groove proximal to said first and second collars.

11. The tunneling device of claim 10, wherein the handle includes an actuator, said actuator configured engage and disengage said handle from one of said first tip and said second tip.

12. The tunneling device of claim 11, wherein said handle includes a shaft and a spring positioned between said shaft and said actuator, wherein said actuator is configured to compress said spring and move said shaft to a position wherein said one of said first tip and said second tip is insertable into or releasable from said handle.

13. The tunneling device of claim 11, wherein said handle includes a post and a spring positioned between said post and said actuator, said post having a first diameter and a second smaller diameter,
said post initially engaging said annular groove of one of said first tip and said second tip inserted in said handle preventing said one of said first tip and said second tip from being removed from said handle, and
said spring biasing said post inwardly positioning said second diameter of said post adjacent to said one of said first tip and said second tip allowing said one of said first tip and said second tip to be removed from said handle.

14. A tunneling device for creating a pathway in subcutaneous tissue of a person's body, said tunneling device comprising:
a flexible member having a first end and a second end, wherein said first end of said flexible member includes a threaded hole;
a first collar rotatably fastened to said first end of said flexible member allowing rotation of said first collar about a longitudinal axis of said first end;
a cap screw having a head and a shaft, said shaft coupled with said threaded hole and a protruding portion of said shaft extending from said threaded hole to said head;
said first collar having a clearance hole extending through a portion of said first collar and including threads opposite said clearance hole; and
a first tip, threaded into said threads of said first collar, the protruding portion of said shaft extending through said clearance hole to rotatably fasten said first collar to said first end of said flexible member, wherein said first tip includes a tapered insertion surface and an annular groove between said tapered insertion surface and said first collar.

15. The tunneling device of claim 14, further comprising:
a second collar rotatably fastened to said second end of said flexible member allowing rotation of said second collar about a longitudinal axis of said second end; and
a second tip fastened to said second collar, said second tip including a second tapered insertion surface and a second annular groove between said second tapered insertion surface and said second collar.

16. The tunneling device of claim 14, further comprising:
a handle configured to removably connect to said annular groove of said first tip.

17. The tunneling device of claim 16, wherein said handle further includes an opening and an engagement shaft having a first diameter and a second larger diameter, said engagement shaft extending through said handle, said engagement shaft configured to move between a first position and a second position within said handle, in said first position said first diameter is positioned across said opening in said handle allowing said first tip to be inserted into said opening of said handle, in said second position said second larger diameter is positioned across said opening and engages said annular groove of said first tip preventing said first tip from being removed from said opening of said handle.

18. The tunneling device of claim 14, further comprising:
a coupler configured to removably connect said first tip and an end of a cable of an implant device securing said flexible member and said cable together, said coupler including a first connector configured to secure said coupler to said end of said cable, and a second connector configured to secure said first tip to said coupler.

19. The tunneling device of claim 14, wherein said flexible member further includes a first tapered insertion surface adjacent to said first end.

20. The tunneling device of claim 19, wherein said flexible member further includes a second tapered insertion surface adjacent to said second end.

* * * * *